US00PP27411P2

(12) United States Plant Patent
Hansen et al.

(10) Patent No.: US PP27,411 P2
(45) Date of Patent: Nov. 22, 2016

(54) ***MISCANTHUS* PLANT NAMED 'AUTUMN ANTHEM'**

(50) Latin Name: *Miscanthus sinensis*
Varietal Denomination: Autumn Anthem

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens Inc., Zeeland, MI (US)

( * ) Notice: Subject to any disclaimer, the term of this patent is extended or adjusted under 35 U.S.C. 154(b) by 104 days.

(21) Appl. No.: 14/544,454

(22) Filed: Jan. 8, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Susan McCormick Ewoldt

(57) ABSTRACT

A new and distinct cultivar of ornamental *Miscanthus sinensis* plant named 'Autumn Anthem' useful in the landscape en masse, small group or single specimen with dense upright culms and arching foliage having dark green summer color and white midribs. The flower habit is a tall dome outline emerging in late summer and effective through the winter changing from a silly pink to airy creamy tan-colored.

1 Drawing Sheet

Botanical classification: *Miscanthus sinensis.*
Variety denomination: 'Autumn Anthem'.

BACKGROUND AND CROSS REFERENCE TO RELATED PLANTS

The present invention relates to the new and distinct plant cultivar of *Miscanthus sinensis* named 'Autumn Anthem', hereinafter also referred to as 'Autumn Anthem' and the "new plant" which represents a new and distinct cultivar of ornamental maiden grass for landscape and cut foliage and flower use. The seed was the result of open pollination between *Miscanthus sinensis* 'Nippon' (not patented) as the female or seed parent and the male or pollen parent is unknown but may have been any one of a number of cultivar or seedling selections in the breeding area. Seed was collected by the inventors in late summer of 2010 at a wholesale perennial nursery in Zeeland, Mich., USA. During initial evaluation in the summer of 2011 and afterward the seedling was assigned the breeder code of KH10-11-01. Final evaluation of the single original seedling was performed at the same nursery in Zeeland, Mich. in the summer and fall of 2012.

The new plant has been successfully asexually propagated by division and sterile plant tissue culture at the same perennial plant nursery in Zeeland, Mich. and found to produce stable and identical plants that maintain the unique characteristics of the original plant. The plant is stable and reproduces true-to-type in successive generations of asexual reproduction.

*Miscanthus* 'Autumn Anthem' differs from its parents as well as all other *Miscanthus* known to the applicant. The new plant differs from the seed parent *Miscanthus* 'Nippon' primarily in the flowering long dome effect that covers the top two-thirds of the plant. The flower dome of 'Nippon' is shorter and covers closer to the top one-quarter.

The nearest other comparison cultivars known to the inventors include: 'Gracillimus' (not patented), 'Huron Sunrise' (not patented) and 'Malepartus' (not patented). 'Gracillimus' is thinner finer textured foliage and flowers later in the season. 'Huron Sunrise' is likewise later flowering, but has thicker coarser leaves than the new cultivar. 'Melepartus' is earlier flowering than 'Autumn Anthem' and also differs in having burgundy tinted foliage. All of the above listed comparison cultivars are also taller than 'Autumn Anthem'.

SUMMARY AND GENERAL DESCRIPTION OF THE PLANT

The new plant is different from all *Miscanthus sinensis* cultivars known to the applicant in the following combined traits:

1. Dense upright culms with arching foliage.
2. Leaves in summer are dark green with a narrow near white midrib.
3. Flowers emerge in late summer and are effective through the winter.
4. Flowering habit is dense and at varying heights creating a tall dome outline.
5. Overall flower effect begins maize-colored, then opens to a light greyed purple and finally seed heads produce an airy light greyed yellow effect.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color. The plant in the photographs is a three-year old plant grown in full-sun trial garden.

DETAILED BOTANICAL DESCRIPTION

Figure 1:
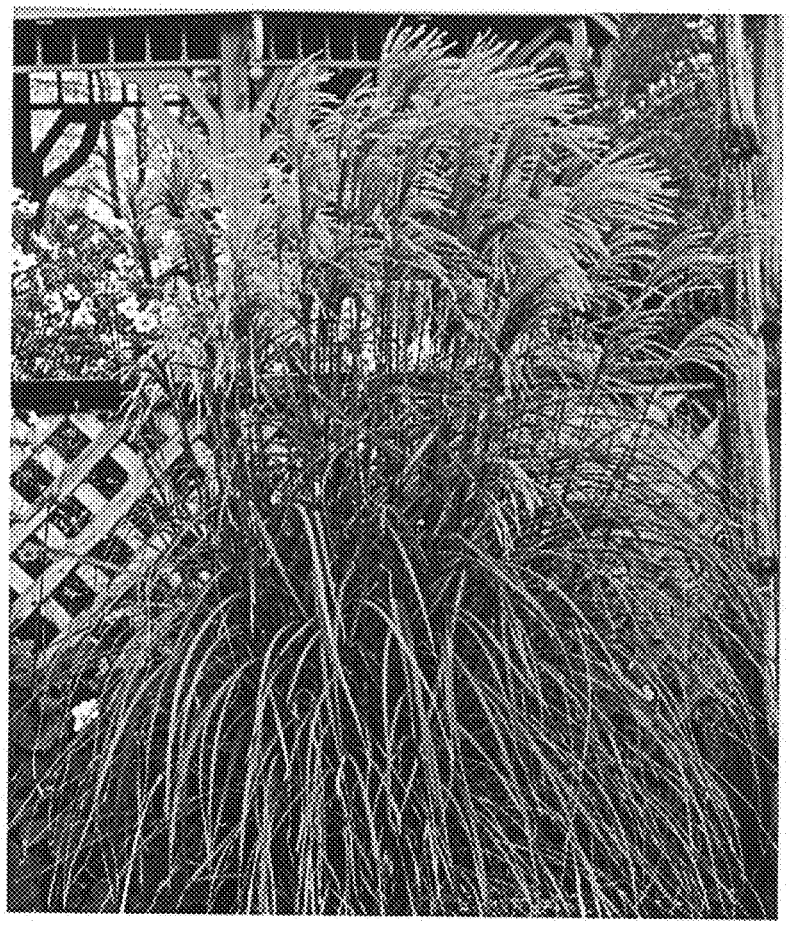
FIG. 1 shows the overall plant in mid fall.
Figure 2:
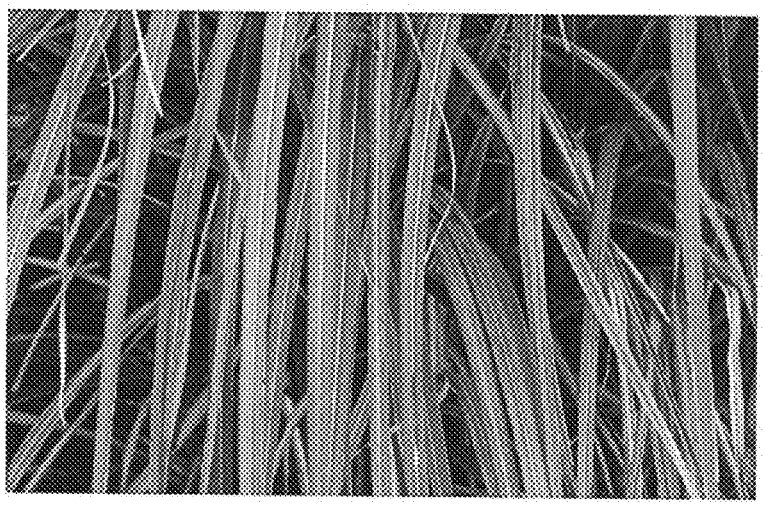
FIG. 2 shows the a close-up of the foliage in mid-fall.

The following descriptions and color references are based on the 2001 edition of The Royal Horticultural Society Colour Chart except where common dictionary terms are used. The new plant, 'Autumn Anthem', has not been observed under all possible environments. The phenotype may vary slightly with different environmental conditions, such as temperature, light, fertility, moisture and maturity levels, but without any change in the genotype. The following observations and size descriptions are of a three-year-old plant in a trail garden in Zeeland, Mich. in full sun with supplemental water and fertilizer.

Parentage: *Miscanthus sinensis* 'Nippon' (not patented) (female, seed)×unknown pollen parent.

Propagation method: By division of the culms and by shoot tissue culture.

Time to finishing in a three-liter pot: About three months.

Rooting habit: Normal, fibrous, coarse, branching.

Plant description: Hardy herbaceous perennial forming tightly rhizomatous clump, with upright culms and arching leaves producing a medium landscape texture through summer and fine flowering texture through winter.

Plant size: Foliage height before flowering is about 90 to 100 cm tall from soil line to the top of the leaves and about 35 to 45 cm wide at soil line, about 140 to 150 cm at mid-level of flowering dome and about 140 to 150 cm tall to top of flowers.

Foliage description: Glaucous, glabrous, entire except microscopically serrulate, linear, conduplicate along center vein, alternate, arching from sheath to apex; sheathed from node of attachment to ligule; deciduous but persist through winter.

Foliage size: Total length about 60.0 to 70.0 cm long, averaging about 66.0 cm; length of sheath average about 18.0 cm, average length of blade about 48.0 cm long; average about 6.5 mm wide.

Foliage color: Changing through the season and with seasonal development, young expanding foliage nearest RHS 144A both surfaces; mature foliage N138A on top and RHS 138A underneath; winter color lighter than RHS 199D.

Color at ligule: Between RHS 163B and RHS 163C on upper leaves, between RHS 144B and 144C in upper leaves.

Veins: Parallel; center vein about 2.0 mm wide.

Vein color: Center vein nearest RHS 155C both top and bottom; other veins same as the surrounding leaf on both the top and bottom of the leaf.

Culm: Glaucous, glabrous, erect, cylindrical, completely enclosed by leaf sheath, about 80 to 100 cm long to panicles and about 5.0 mm diameter at base; internode length 8 to 27 cm, shorter near base, average about 14.8 cm.

Culm color: Changes with seasons; early-season nearest RHS 145C, mid-season nearest RHS 138A, later-season after flowering between RHS 199C and RHS 199B.

Nodes: Swollen, lower nodes to about 7.0 mm diameter, glabrous; covered by sheath.

Ligule: Fringed membranous, 2.0 mm long and as wide as leaf; with fine hairs to 5.0 mm long.

Ligule color: Nearest RHS 163B; drying to nearest RHS 165D; hair color RHS 165D.

Flower description: Spikelets in pairs on branched panicle, one panicle per culm, beginning early to mid-September, drying on plant but persisting through winter; no fragrance detected.

Panicle: About 30 to 35 cm long, 30 to 32 cm wide at widest portion; with about 20 branches; branches to about 17.0 cm long.

Panicle color: Beginning nearest RHS 184C and developing to RHS 161C.

Spikelet: With tufts of fine hairs about 5.0 mm long and about 0.1 mm diameter at base and along sides of paired glumes.

Pedicle: About 2.5 mm long and less than 0.5 mm diameter; color nearest RHS 166C.

Lemma: Of about equal size and color to palea; about 4.5 mm long and about 1.0 mm wide; base truncate with tufts of hairs; apex narrowly acute; margin entire with hairs of equal size to basal tuft; color nearest RHS 163C; hair color collectively nearest RHS 158C.

Palea: Matched to lemma in size, shape, hairs and color.

Awn: Thin, bristle, about 9.0 mm long; color between RHS 166C and RHS 166D.

Gynoecium: Two.

*Stigma*.—Two, plumose, protruding about 2 mm from glume; color nearest RHS 183C.

Androecium:

*Filaments*.—Fine, hair-like, white, about 2.0 mm long and about 0.3 mm diameter.

*Anthers*.—Oblong; about 3.0 mm long and 1.0 mm diameter; color nearest RHS 183B.

*Pollen*.—Abundant; color nearest RHS 16C.

Fruit: Caryopsis; enclosed in glume; about 2 to 3 mm long and about 0.5 mm diameter, nearest RHS 164C.

Hardiness, pest and disease resistance: The plant grows best with plenty of moisture and adequate drainage, but is able to tolerate considerable drought when established.

Hardiness at least from USDA zone 5 through 9. Disease and pest resistance beyond what is typical of that of other Maiden Grasses has not been observed.

We claim:

1. A new and distinct cultivar of ornamental *Miscanthus sinensis* plant named 'Autumn Anthem' as herein described and illustrated.

* * * * *